United States Patent
Trofimov et al.

(10) Patent No.: US 11,083,770 B2
(45) Date of Patent: Aug. 10, 2021

(54) MEDICAL PREPARATION AND METHOD FOR ENHANCING TISSUE OXYGENATION IN CASE OF DIABETIC FOOT

(71) Applicant: Omnipep Establishment, Vaduz (LI)

(72) Inventors: Aleksandr Vladislavovich Trofimov, Saint-Petersburg (RU); Vladimir Khatskelevich Khavinson, Saint-Petersburg (RU); Oleg Mikhailovich Ivko, Almaty (KZ); Svetlana Vladislavovna Trofimova, Saint-Petersburg (RU)

(73) Assignee: Omnipep Establishment, Vaduz (LI)

( * ) Notice: Subject to any disclaimer, the term of this patent is extended or adjusted under 35 U.S.C. 154(b) by 0 days.

(21) Appl. No.: 16/634,973

(22) PCT Filed: Nov. 8, 2017

(86) PCT No.: PCT/RU2017/000837
§ 371 (c)(1),
(2) Date: Jan. 29, 2020

(87) PCT Pub. No.: WO2019/093918
PCT Pub. Date: May 16, 2019

(65) Prior Publication Data
US 2020/0237850 A1    Jul. 30, 2020

(51) Int. Cl.
*A61K 38/05* (2006.01)
*A61P 17/02* (2006.01)
*C07K 5/06* (2006.01)

(52) U.S. Cl.
CPC ............... *A61K 38/05* (2013.01); *A61P 17/02* (2018.01)

(58) Field of Classification Search
CPC ........... A61K 38/05; A61P 17/02; C07K 5/06; C07K 5/06104
USPC ............................................. 514/21.91, 1.1
See application file for complete search history.

(56) References Cited

U.S. PATENT DOCUMENTS 5,770,576 A * 6/1998 Morozov ............... A61K 38/05
514/13.5

FOREIGN PATENT DOCUMENTS

RU    2165767 C1    4/2001
RU    2228763 C1    5/2004

OTHER PUBLICATIONS

Anisimov et al., "Immunomodulatory synthetic dipeptide L-Glu-L-Trp slows down aging and inhibits spontaneous carcinogenesis in rats," Biogerontology, 2000, 1: 55-59. (Year: 2000).*
Maxim Shevtsov, et al: "Glu-Trp-ONa or its acylated analogue (R-Glu-Trp-ONa) administration enhances the wound healing in the model of chronic skin wounds in rabbits", Drug Design, Development and Therapy, vol. 9, Mar. 1, 2015, pp. 1717-1727.
David G. Armstrong, et al: "Diabetic Foot Ulcers and Their Recurrence", New England Journal of Medicine, vol. 376, No. 24, Jun. 15, 2017, pp. 2367-2375.
Sergiu-Bogdan Catrina et al: "Disturbed hypoxic responses as a pathogenic mechanism of diabetic foot ulcers: HIF-1 and Wound Healing in Diabetes", Diabetes/Metabolism Research and Reviews, vol. 32, Jan. 1, 2016, pp. 179-185.
International Search Report and Written Opinion issued in International Application No. PCT/RU2017/000837 dated Jul. 17, 2018.

* cited by examiner

*Primary Examiner* — Julie Ha
(74) *Attorney, Agent, or Firm* — Hoffmann & Baron, LLP

(57) ABSTRACT

A method and medical preparation for enhancing tissue oxygenation by suppression of a hypoxia induced factor 1α (HIF-1α) in case of low oxygen tension in a tissue of a diabetic foot in a patient with type I or type II diabetes mellitus, wherein the method includes administering a dipeptide of L-glutamic acid-L-tryptophan (L-Glu-L-Trp), and wherein the medical preparation includes an effective amount of the dipeptide of L-Glu-L-Trp as an active agent and a pharmaceutically acceptable carrier. Moreover, the method can include administering the medical preparation in a dose of 1.0 µg per kg-10.0 µg per kg of body weight at least once a day for a period necessary to achieve a therapeutic effect.

5 Claims, No Drawings

MEDICAL PREPARATION AND METHOD FOR ENHANCING TISSUE OXYGENATION IN CASE OF DIABETIC FOOT

CROSS-REFERENCE TO RELATED APPLICATIONS

The present application is the U.S. National Phase of PCT/RU2017/000837, filed on 8 Nov. 2017, the entire contents of which are incorporated herein by reference.

BACKGROUND

Technical Field

The invention relates to medicine and can be used for enhancing tissue oxygenation in case of complications of diabetes mellitus, in particular, in case of diabetic foot.

Related Art

The problem of treatment for complications of diabetes mellitus remains challenging in modern medicine, in particular in diabetology. According to the World Health Organization, the number of patients with diagnosed diabetes mellitus is presently about 160 million people, and the number of patients with this diagnosis is expected to be doubled by 2025. One of the complications of diabetes mellitus is a "diabetic foot" syndrome. This complication is manifested by a complex of anatomic and functional changes which lead to the development of tissue ischemia (hypoxia) accompanied by increased traumatization and infection of foot soft tissues.

It should be noted that such complications lead to early disablement of patients, and eventually to foot amputation and death. Basic mechanism of tissue ischemia development in case of diabetes mellitus consists in the activation of HIF-1α factor (specific regulatory protein-hypoxia induced factor). Pathogenic role of HIF-1α factor reveals a possibility of not only correcting hypoxia per se, but also of a treatment for complications of diabetes mellitus, such as "diabetic foot". Therefore, development of pharmacological therapy that is aimed at activating soft tissues oxygenation by inhibiting HIF-1α factor synthesis is a vital task for medicine and a pathogenetic approach to the treatment for complications of diabetes mellitus.

There is known a group of medical preparations with an antihypoxic effect, inhibiting the synthesis of a specific regulatory protein-hypoxia induced factor (HIF 1α): trastuzumab (herceptin), geftinib, calphostin C (protein kinase C inhibitor), wortmannin (PI3K inhibitor), PD98095 (MAPK inhibitor), rapamycin (sirolimus, FRAP/mTOR inhibitor), sorafenib and sunitinib (multi-kinase inhibitors), noscapin (see Nilsson M. B., Zage P. E., Zeng L. et al.). Multiple receptor tyrosine kinases regulate HIF 1α and HIF 2α in normoxia and hypoxia in neuroblastoma: implications for antiangiogenic mechanisms of multikinase inhibitors//Oncogene.-2010.-Vol. 29.-P. 2938-2949; Y. S. Chang, L. Adnane, A. Henderson et al. Sorafenib (bay43-9006) inhibits tumor growth and vascularization and induces tumor necrosis in the human rcc xenograft model, 786-o//Clin. Cancer. Res.-2005.-Vol. 11.-P. 9011; Zhang H., Qian D. Z., Tan Y. S. et al. Digoxin and other cardiac glycosides inhibit HIF 1 synthesis and block tumor growth//PNAS.-2008.-Vol. 105, N 50.-P. 19579-19586; Newcomb E. W., Lukyanov Y., Schnee T. etc. Noscapine inhibits hypoxia-mediated HIF 1alpha expression and angiogenesis in vitro: a novel function for an old drug//Int. J. Oncol.-2006.-Vol. 28, N 5.-P. 1121-1130).

The above-mentioned preparations have a drawback of being toxic to different extents, which manifests itself in the development of side effects: hypertension, blood coagulation system disorders, cardiac incompetence, gastrointestinal (nausea, vomit, and diarrhea), neurological (weakness, headache), and dermatological symptoms (skin rash) as described by Llovet et al. (see J. M. Llovet, S. Ricci, V. Mazzaferro et al. Sorafenib in advanced hepatocellular carcinoma//N. Engl. J. Med.-2008.-Vol. 359.-P. 378-390.

The U.S. Pat. No. 5,811,399 (published by Sep. 22, 1998) disclosed dipeptide L-Glu-L-Trp being a result of peptide synthesis.

Medical preparation named "Thymogen" (dipeptide L-Glu-L-Trp), which is approved for therapeutic usage in the Russian Federation (registration number R N 002408/01) and is listed in the Russian Pharmacopoeia, is known to reveal an immunomodulating activity and to influence cellular and humoral immunity reactions as well as non-specific resistance of the body as a whole (see patent U.S. Pat. No. 5,538,951 published by Jul. 23, 1996). However, the known activity of the said dipeptide characterizes the immunomodulating effect, which is not an apparent and consistent manifestation of capacities of the peptide to inhibit the synthesis of HIF-1α factor and enhance tissue oxygenation in case of insulin-dependent and non-insulin-dependent diabetes mellitus, and does not define specific indications for its clinical usage. Examples of antihypoxic effect of dipeptide L-Glu-L-Trp in enhancing tissue oxygenation in case of complications of diabetes mellitus and, in particular, in case of diabetic foot, provided herein below, objectively confirm the absence of interconnection between its known capacity and the claimed one.

SUMMARY

Thus, an object of the claimed invention consists in providing a peptide medical preparation, which exerts an antihypoxic effect and is capable of enhancing tissue oxygenation in case of complications of diabetes mellitus and, in particular, in case of diabetic foot, by way of inhibiting HIF-1α factor synthesis.

The object is achieved by using of a dipeptide L-Glu-L-Trp as a means for enhancing tissue oxygenation by suppression (reducing a synthesis) of HIF-1α factor in case of diabetic foot.

The dipeptide may be obtained by standard method of peptide synthesis in a solution as described for example in U.S. Pat. No. 5,538,951 (published by Jul. 23, 1996).

The other aspect of the invention is a medical preparation for enhancing tissue oxygenation by suppression (reducing a synthesis) of HIF-1α factor in case of diabetic foot, comprising an effective amount of dipeptide L-Glu-L-Trp as an active agent and a pharmaceutically acceptable carrier.

The term "medical preparation" as used herein implies the use of any formulation which comprises different pharmaceutical derivatives of the dipeptide that exert a therapeutic effect for the treatment of complications of diabetes mellitus, for which enhanced tissue oxygenation is necessary.

The term "effective amount" as used herein implies the use of an amount of the active agent, which must be effective in a given formulation, according to its quantitative values of activity and toxicity, as well as based on the knowledge of a person skilled in the art.

In some embodiments, dipeptide L-Glu-L-Trp may be used in form chemical modification, e.g., different salts and other derivatives, well known for the persons skilled in the art.

In order to obtain pharmaceutical compositions according to the invention, the dipeptide L-Glu-L-Trp or its pharmaceutically acceptable derivatives are mixed as an active ingredient with a pharmaceutical carrier according to compounding techniques that are used in pharmaceutics.

The carrier may take different forms depending on the drug formulation which is desired to be administered into the body, e.g., for parenteral, intranasal, oral, or local (e.g., in the form of applications or ointment).

Any known pharmaceutical components may be used in the manufacture of compositions in a preferred dosage form for oral or local administration.

For parenteral (intranasal) administration, the carrier normally includes sterile water, although other ingredients which promote stability or preserve sterility may also be included.

In preferred embodiments of the claimed invention, the proposed medical preparation is used in the form of a drug formulation for local administration.

For the local administration, the carriers comprise aqueous solutions, e.g., saline solution.

In one preferred embodiment of invention, pharmaceutically acceptable carrier is a saline solution.

According to the invention, the dipeptide is active when administered in the doses of 1.0 µg/kg-10.0 µg/kg of body weight, although lower or higher doses may also be used depending on the severity and course of the disease.

The invention also provides a method for enhancing oxygenation processes in a human or animal in need of such stimulation, in particular, a method of enhancing tissue oxygenation by suppression (reducing a synthesis) of HIF-1α factor in case of a diabetic foot.

According to the invention, a method for enhancing oxygenation processes, in case of complications of diabetes mellitus, in particular, in case of diabetic foot includes administering the medical preparation, comprising an effective amount of dipeptide L-Glu-L-Trp as an active agent and a pharmaceutically acceptable carrier in the dose of 1.0 µg per kg-10.0 µg per kg of body weight at least once a day for a period necessary to achieve a therapeutic effect.

Enhancing oxygenation processes is realized by inhibiting the synthesis of specific regulatory protein-hypoxia induced factor (HIF 1a), which leads to enhanced tissue oxygenation against the background of insulin-dependent and non-insulin-dependent diabetes mellitus.

In one embodiment of invention, the period necessary for achieving the therapeutic effect is from 10 days to 40 days depending on the nature and severity of the disease.

This invention will become clear in terms of several embodiments given below.

DETAILED DESCRIPTION

The invention is illustrated by an example of synthesis of dipeptide with formula L-glutamic-L-tryptophan acid (L-Glu-L-Trp) (Example 1), by examples of testing toxicity and biological activity of the dipeptide (Examples and 3), and examples of results of clinically administering the dipeptide which demonstrate its pharmaceutical properties and confirm the possibility of achieving the therapeutic effect (Examples 4 and 5).

It should be noted that the subsequent description of these embodiments is illustrative and not exhaustive.

Example 1

Synthesis of R'-Glu-Trp-R"

Conveniently, the dipeptide R'-Glu-Trp-R" is synthesized by any of a number of automated techniques that are now commonly available. Generally speaking, these techniques involve stepwise synthesis by successive additions of amino acids to produce progressively larger molecules. The amino acids are linked together by condensation between the carboxyl group of one amino acid and the group of another amino acid to form a peptide bond. To control these reactions, it is necessary to block the amino group of one amino acid and the carboxyl group of the other.

The blocking groups should be selected for easy removal without adversely affecting the peptides, i.e., by racemization or by hydrolysis of the formed peptide bonds. Amino acids with carboxyl-groups (e.g., Asp and Glu) or hydroxyl-groups (e.g., Ser, homoserine, and Tyr) also require blocking prior to condensation. A wide variety of procedures exists for synthesis of peptides, solid-phase synthesis usually being preferred. In this procedure, an amino acid is bound to a resin particle, and the peptide generated in a stepwise manner by successive additions of protected amino acids to the growing chain. Modifications of the technique described by Merrifield are commonly used (see Merrifield, R. B., J. Am. Chem. Soc. 96:2989-2993 (1964)).

In an example automated solid-phase method, peptides are synthesized by loading the carboxy-terminal amino acid onto an organic linker (e.g., PAM, 4-oxymethyl phenylacetamidomethyl) covalently attached to an insoluble polystyrene resin that is cross-linked with divinyl benzene. Blocking with t-Boc is used to protect the terminal amine, and hydroxyl- and carboxyl-groups are commonly blocked with O-benzyl groups. Synthesis is accomplished in an automated peptide synthesizer (Applied Biosystems, Foster City, Calif., e.g., Model 430-A). Following synthesis, the product may be removed from the resin and blocking groups removed using hydrofluoric acid or trifluoromethyl sulfonic acid according to established methods (see Bergot, B. J., McCurdy S. N., Applied Biosystems Bulletin (1987)).

A routine synthesis can produce 0.5 mmole of peptide-resin. The yield following cleavage and purification is approximately 60% to 70%. For example, an amino and side chain protected derivative of an activated ester of Glx is reacted with side-group protected Trp, attached to the solid phase at its C-terminus. After elimination of the alpha-amino protecting group, the peptide may be cleaved from the solid phase or another amino acid added in a similar fashion. Additional amino acids are serially added in a similar fashion. The peptides are then cleaved by acid that also typically removes protecting groups. The peptides may then be isolated and lyophilized and stored for future use. Suitable techniques of peptide synthesis are described in detail in Stewart J. M., Young J. D. Solid phase peptide synthesis, 2d edition, 1984; and Tam, et al., J. Am. Chem. Soc. 105:6442, 1983, both of which are incorporated herein by reference.

Purification of the product peptides is accomplished, for example, by crystallizing the peptide from an organic solvent such as methyl-butyl ether, followed by dissolving in distilled water, and dialysis (if the molecular weight of the peptide is greater than about 500 daltons), thin layer chromatography, gel chromatography, lyophilization, or reverse HPLC (e.g., using a C18 column with 0.1% trifluoroacetic acid and acetonitrile as solvents) if the molecular weight of the peptide less than 500 daltons. Purified peptide is lyophilized and stored in a dry state until use. A representative R'-Glu-Trp-R" pharmaceutical preparation is the purified dipeptide L-Glu-L-Trp, which comprises a white powder (if lyophilized; otherwise, it is crystalline), soluble in water, DMF; insoluble in chloroform and ether. [alpha$22_D$=+12.6; C=0.5 $H_2O$. $R_f$=0.65 (butanolzacetic acid:water=3:1:1). UV (275±5 nm, max). NMR (500 MHz): 0.001 mol/l of the peptide solution, Trp (3.17; 3.37; 4.57; 7.16; 7.24; 7.71; 7.49); Glu (1.90; 1.96; 2.21; 3.72)].

Typically, an amino and side chain protected derivative of an activated ester of glutamic acid is reacted with protected L-tryptophan. After elimination of the protecting groups and conventional purification, such as by thin layer or GL chromatography, the peptide may be purified such as by, lyophilization, gel purification, and the like.

Example 2

Study of Toxicity of Dipeptide L-glutamic-L-tryptophan Acid (L-Glu-L-Trp).

General toxicity of dipeptide L-glutamic-L-tryptophan acid (L-Glu-L-Trp) was carried out in accordance with the "Guidelines for preclinical assessment of safety of pharmacological preparations (GLP)" and all animals were maintained in accordance with European Directive 86/609/EC (5 Council of the European Communities. Council Directive 86/609/EEC of 24 Nov. 1986 on the approximation of laws, regulations and administrative provisions of the Member States regarding the protection of animals used for experimental and other scientific purposes. Off J Eur Communities L358:1-28).

Experimental protocols were adopted by the Commission on Humane Treatment of Animals of the St. Petersburg Institute of Bioregulation and Gerontology (Russia).

The study was aimed at determining the tolerable toxic doses of the preparation, evaluating the extent and nature of pathologic changes in various organs and tissues of the organism, and identifying the dependency of toxic effects on the dose and duration of administration of the preparation.

Acute toxicity of dipeptide L-Glu-L-Trp was identified using the Kerber's method. The study was carried out on 60 white mongrel male mice with body weight of 20-25 g, which were maintained according to a standard regimen and received standard nutrition in a vivarium. The animals were randomly distributed into 6 equal groups, 10 mice in each. The preparation was administered to the animals once, intramuscularly, in the volume of 0.25 ml, in the doses of 1 mg/kg, 2 mg/kg, 3 mg/kg, 4 mg/kg, and 5 mg/kg (exceeding the therapeutic dose recommended for clinical study by several thousand times). Control group animals were administered saline solution in the same volume.

Death of animals did not take place in any of the groups within 72 hours and in further 14 days. No changes in general state, behavior, motion activity, hair and skin, bowel, and bladder functions of the animals were observed.

Thus, dipeptide L-Glu-L-Trp does not cause acute toxic reactions in doses which exceed the therapeutic one, which is recommended for clinical studies, by several thousand times, which points out a broad margin of safety of the preparation.

Study of sub-acute toxicity of dipeptide L-Glu-L-Trp was carried out on 60 white mongrel rats with body weight of 150-250 mg. The animals of experimental groups received the preparation intramuscularly, for 90 days, in the doses of 1 µg/kg, 0.3 mg/kg, and 3 mg/kg in 0.5 ml of saline solution. Control animals received saline solution in the same volume.

Animals were under daily observation during the whole period of the study. Behavior of the animals, food and water consumption, state of hair and mucous coats were monitored. The animals were subjected to daily weighing. Morphological composition and properties of peripheral blood in the animals were studied before the administration of the preparation, on the 30th, 60th, and 90th day after the beginning of administration of the preparation. Blood biochemistry and coagulation indices were studied upon completion of the experiment.

Chronic toxicity of dipeptide L-Glu-L-Trp obtained by the claimed method was studied by its long-term administration to rats with body weight of 150 mg-250 mg. The preparation was administered to the animals daily, intramuscularly, in the doses of 1 µg/kg, 0.1 mg/kg, and 1 mg/kg in 0.5 ml of saline solution for 6 months.

Behavior of the animals, food and water consumption, state of hair and mucous coats were monitored. The animals were subjected to weighing daily during the first 3 months of the experiment and then once a month. Three months after the beginning of administration and upon completion of the experiment, hematology and biochemistry studies were carried out. Cardiovascular system, liver, pancreas, kidney, and adrenal glands functions were assessed. After the completion of administration of the preparation, some of the animals were subjected to a pathomorphological study for the purpose of assessing the state of different parts of the brain and spinal cord, heart, aorta, lungs, liver, kidneys, endocrine, and immune system organs.

Evaluation of the general state of the animals, peripheral blood morphology and biochemistry indices, morphological state of the internal organs, the state of cardiovascular and respiratory systems, liver and kidney functions did not reveal any pathologic changes in the organism.

Studies of acute and sub-acute toxicity of dipeptide L-Glu-L-Trp point out the absence of side effects from long-term administration of the preparation in the doses that exceed the therapeutic dose by 100-1000 times.

Example 3

Effect of dipeptide L-Glu-L-Trp on the activation of oxygenation and, as a consequence, on wound healing in soft tissues against the background of streptozotocin-induced diabetes mellitus (treatment).

The experiment was carried out on 30 Wistar line population male rats. The streptozotocin model is one of the most suitable for use in wound healing studies, allowing accurate quantification of the main aspects of a healing wound such as wound closure, reepithelialization, and GT (granulation tissue) formation (see Hirsch T., Spielmann M., Zuhaili B. et al. Enhanced susceptibility to infections in a diabetic wound healing model//BMC Surgery.-2008.-Vol. 8(5).-P.1-8 and Mendes J., Leandro C., Bonaparte D. et al. A Rat Model of Diabetic Wound Infection for the Evaluation of Topical Antimicrobial Therapies//Comparative Medicine.-2012.-Vol. 62 (1).-P.37-48). The excisional wound model accommodates the broadest assessment of the mechanisms involved in wound healing, including epithelialization, granulation, and angiogenesis (see Wong V. W., Sorkin M., Glotzbach J. P., Longaker M. T., Gurtner G. C. Surgical approaches to create murine models of human wound healing//J Biomed Biotechnol.-2011:969618.; Toker S., Gulcan E., Cayc M. K., Olgun E. G., Erbilen E., Ozay Y. Topical atorvastatin in the treatment of diabetic wounds//Am J Med Sci.-2009.-Vol. 338.-P. 201-204; and Tsuboi R., Rifkin D. B. Recombinant basic fibroblast growth factor stimulates wound healing in healing-impaired db/db mice//J Exp Med.-1990.-Vol. 172.-P. 245-251)

The rats were maintained in microisolation caging in a room with controlled humidity (50% to 70%) and temperature (20° C. to 22° C.), a 14:10-h light:dark cycle, and free access to pelleted rodent chow (RM3, Special Diet Systems, Essex, UK) and filter-sterilized water. The animals were maintained in accordance with the Good Laboratory Practice (GLP) Guidelines and all animals were maintained in accordance with European Directive 86/609/EC.

Experimental protocols were adopted by the Commission on Humane Treatment of Animals of the St. Petersburg Institute of Bioregulation and Gerontology (Russia).

The animals were randomly divided into two groups—control (n=15) and experimental (n=15). Experimental pathology was formed in experimental and control animals by a single intraperitoneal administration of streptozotocin (Sigma, US) in the dose of 60 mg/kg.

To identify biochemical and histological manifestations of diabetes and its late complications, dynamic study was performed in all animals (peripheral blood glucose and reticulocytes were evaluated), and histological studies were also performed. Effect of dipeptide L-Glu-L-Trp on the activation of tissue oxygenation was assessed in an immunohistochemical study. This method enables analyzing HIF-$1\alpha$ protein content in tissues of control and experimental group animals.

Glucose concentration in peripheral blood (in the caudal vein) was measured by a glucose meter OneTouch Horizon ("Lifescan", US). Linear range of measurement was 1.1 mmole/l-33.3 mmole/l. Reticulocytes count was carried out using a unified technique after their staining with a ready dye—brilliant cresyl blue (Diachem-HemiStain-RTC) in a test tube (supravital staining method in a test tube).

Skin tissues of control and experimental group animals were taken for histological and immunohistochemical studies. The material was fixed in a 10% neutral formalin solution for 24 hours and embedded in paraffin using a standard technique. Slices of 5-7 μm thickness were then produced, and stained with hematoxylin and eosin for histological studies. Morphological study of histological preparations was carried out using a light-optical microscope CarlZeiss (Germany).

Immunohistochemical study included an identification of HIF-$1\alpha$ factor expression. Obtained paraffin blocks were cut on a microtome. Slices were dewaxed (paraffin was removed). Primary rabbit polyclonal antibodies to HIF-$1\alpha$ were applied to the slices at a dilution of 1:100 and incubated overnight at +40° C. in a humid chamber. Then the slices were treated with secondary biotinylated goat anti-rabbit antibodies (at a dilution of 1:200) for 30 minutes at a room temperature in a humid chamber. Then they were rinsed, and a universal system of avidin-biotin complex (ABC, Vector Laboratories, Inc, USA) was applied, and left for incubation for 30 minutes at room temperature. Diaminobenzidine kit (DAB Substratekit, VectorLabs, USA) was used to visualize the reaction of binding between antibody and antigen. Microphotography was performed using a digital photo camera ProgressCT1 ("Jenoptic", Germany). Preparations were analyzed using a morphometric station which enables quantizing gene products expression by intensity of immune reactivity in standard units of optical density. Morphometric station included a light microscope OlympusCX1 (Japan), digital camera ProgressCT1 ("Jenoptic", Germany), and an IBM PC with a Videotest Master Morfology software. Videotest Master Morfology software was used to count the quantity of immunopositive cells.

The study showed that, after 5 weeks, clinical signs of diabetes mellitus were identified in all animals, which manifested themselves in a statistically significant increase in glucose concentration as compared to the initial indices (by more than 4 times) (see Table 1).

TABLE 1

Glucose concentration dynamics in peripheral blood of male rats

| Duration of study (weeks) | Glucose concentration (mmole/l) | |
|---|---|---|
| | Control group (n = 15) | Experimental group (n = 15) |
| 0 | 5.2 ± 2.0 | 5.7 ± 1.2 |
| 5 | 23.5 ± 1.8* | 24.4 ± 1.9* |
| 9 | 19.4 ± 1.9* | 15.9 ± 2.2* |
| 11 | 18.6 ± 1.7* | 13.4 ± 1.5* |

*$p < 0.05$ - difference is statistically significant as compared to the initial index in the control and experimental groups.

Soft tissue lesion was modeled in all animals on the 5th week against the background of clinical signs of diabetes mellitus. All diabetic rats were anesthetized by intraperitoneal injection of xylazine hydrochloride (10 mg/kg) and ketamine hydrochloride (25 mg/kg). For this purpose, control and experimental animals' hair was shaved in the region of femoral soft tissues, and a 1.0 cm long and 0.3 cm deep cut was made. Soft tissues (muscles and subcutis) were crushed by Kocher's forceps, then the skin was sutured. After 72 hours, the sutures were lifted, and the lesions were treated with 3% hydrogen peroxide solution.

Seventy-two hours after the soft tissue lesion modeling, dipeptide L-Glu-L-Trp was administered to experimental group animals daily, once a day, intramuscularly, in the dose of 100 μg (1.0 mg) per injection, for 10 days. Saline solution was administered to control group animals from the same time and by the similar pattern.

It is known that the specific regulatory protein-hypoxia induced factor (HIF-$1\alpha$)—is a reliable marker of hypoxia. Activity of this factor increases when oxygen load on blood and tissues of the body is reduced. It was shown that this factor plays a key role in the systemic response of the organism to hypoxia (see Semenza G. L. Regulation of oxygen homeostasis byhypoxia-inducible factor 1//Physiology (Bethesda).-2009.-Vol. 24.-P. 97-106). As can be seen in Table 2, a reliable increase in HIF-$1\alpha$ factor expression occurred in all animals on the 5th week of the study against the background of clinical signs of diabetes mellitus. HIF-$1\alpha$ factor is responsible for forming the basis for long-term adaptation to hypoxia. Thus, significant accumulation of HIF-$1\alpha$ in the tissues points out tissue ischemia in the experimental animals.

However, by the 11th week, HIF-$1\alpha$ expression level under the effect of dipeptide L-Glu-L-Trp in the experimental group turned out to be reliably lower than in the control. The obtained data proves that dipeptide L-Glu-L-Trp is capable of enhancing tissue oxygenation.

TABLE 2

HIF-1α expression dynamics in rat cutaneous tissues

| Duration of study (weeks) | Optical density of HIF-1α expression, c.u. | |
|---|---|---|
| | Control group (n = 15) | Experimental group (n = 15) |
| 0 | 0.357 ± 0.032 | 0.360 ± 0.030 |
| 5 | 0.528 ± 0.04* | 0.547 ± 0.042* |
| 11 | 0.519 ± 0.038* | 0.436 ± 0.035#* |

*$p < 0.05$ - difference is statistically significant as compared to the initial index in the control and experimental groups.
$p < 0.05$ - difference is statistically significant as compared to the respective index in the control group.

It is known that oxygen deficiency occurs in tissues against the background of chronic diabetes. Hypoxia enhances HIF-1α expression in tissues, which triggers response physiological reactions, such as angiogenesis, erythropoiesis, and emission of young erythrocytes and reticulocytes to systemic blood circulation (see Semenza G. L. Hypoxia-inducible factor 1: master regulator of 02 homeostasis//Bioch. Pharmacol.-1998.-Vol. 8., N.5.-P. 588-594; and Semenza G. L. Involvement of oxygen-sensing pathways in physiologic and pathologic erythropoiesis.// Blood.-2009.-Vol. 114, N.10.-P. 2015-2019). It was proved that the level of reticulocytes in peripheral blood under oxidation stress reflects the extent of tissue hypoxia (see Wu K., Huan Y. Streptozotocin-induced diabetic models in mice and rats//Curr Protoc Pharmacol.-2008, March-Chapter 5:Unit 5.47.-P. 1-14; Chen D., Wang M. W. Development and application of rodent models for type 2 diabetes// Diabetes Obes. Metab.-2005.-Vol. 7, Ng 4.-P. 307-317 and Srinivasan K., Ramarao P. Animal models in type 2 diabetes research: an overview//Indian J. Med. Res.-2007.-Vol. 125, No 3.-P. 451-472).

After 11 weeks since the modeling of experimental streptozotocin-induced diabetes, statistically significant increase in the level of reticulocytes was identified in all animals of the control group, which is a sign of tissue hypoxia. However, level of reticulocytes in the experimental group under the effect of dipeptide L-Glu-L-Trp turned out to be reliably lower than in the control (Table 3). The resulting data points out that dipeptide L-Glu-L-Trp activates cell metabolism processes in tissues and exerts a regulatory effect on the level of oxidative stress and enhancement of tissue oxygenation.

TABLE 3

Dynamics of reticulocytes content in peripheral blood of male rats

| Duration of study (weeks) | Reticulocytes content (‰) | |
|---|---|---|
| | Control group (n = 15) | Experimental group (n = 15) |
| 0 | 15.5 ± 1.9 | 14.9 ± 1.7 |
| 5 | 19.5 ± 2.8 | 20.4 ± 2.5 |
| 9 | 59.2 ± 8.9* | 26.6 ± 6.2# |
| 11 | 57.6 ± 7.4* | 30.1 ± 5.4#* |

*$p < 0.05$ - difference is statistically significant as compared to the initial index in the control and experimental groups.
$p < 0.05$ - difference is statistically significant as compared to the respective index in the control group.

Histological study data confirmed the existence of changes, which are typical for diabetic pathology, by the 11th week. Typical signs of microangiopathy, which are characteristic for late complications of diabetes, were histologically identified in experimental and control group animals. Productive capillaritis with mild perivascular sclerosis, as well as sclerosis of arteriolar walls were observed in all animals. However, these signs were less pronounced in the experimental group animals than in the control, which indirectly evidences the enhancement of tissue oxygenation. Besides, perivascular lymphohistiocytic infiltration was identified, which was severe to moderate in the control group and mild in the experimental group. Both in the control and the experimental group lymphohistiocytic infiltration partly affected perineural zones. Besides, control group showed a pronounced axonal degeneration, amyelination and focal axonal necrobiosis. Trophic disturbances caused dystrophic disorders in the derm in both groups. However, derm of control group animals showed a significantly more pronounced hyperkeratosis and acanthosis, the process in some cases involving cutaneous appendages (hair follicles, sebaceous and perspiratory glands), than in animals of the experimental group.

Positive effect of dipeptide L-Glu-L-Trp on oxygenation processes in tissues contributed to quicker healing of soft tissue lesions, which shortened the regeneration period, caused the appearance of granulation tissue in the lesion, marginal epithelization or full epithelization (Table 4).

TABLE 4

Effect of dipeptide L-Glu-L-Trp on soft tissue lesion healing against the background of streptozotocin-induced diabetes mellitus

| Duration of study (weeks) | Number of animals with signs of tissue granulation | | Number of animals with signs of beginning of marginal epithelization | | Number of animals with full tissue epithelization | |
|---|---|---|---|---|---|---|
| | Control group (n = 15) | Experimental group (n = 15) | Control group (n = 15) | Experimental group (n = 15) | Control group (n = 15) | Experimental group (n = 15) |
| 5 | 0 | 0 | 0 | 0 | 0 | 0 |
| 9 | 2 (13.3%) | 4 (26.7%) | 1 (6.7%) | 6 (40.0%) | 1 (6.7%) | 5 (33.3%) |
| 11 | 3 (20.0%) | 0 | 3 (20.0%) | 2 (13.3%) | 4 (26.7%) | 13 (86.7%) |

So, study results on the 11th week showed that full epithelization of lesions in the experimental group which received the peptide exceeded the same index in the control group by 3.2 times. Besides, on the 11th week of observation, no signs of lesion surface regeneration were identified in 5 control group animals.

The above examples of clinical study of the claimed dipeptide demonstrate its pharmacological capabilities and confirm the possibility of practicing the invention.

Example 4

Efficacy of dipeptide Thymogen L-Glu-L-Trp administration in the treatment of "diabetic foot" in patients with insulin-dependent diabetes mellitus.

Thirty-five patients with insulin-dependent diabetes mellitus were monitored. All patients suffered from diabetes mellitus for 10 years-23 years, and their age was 25 years to 49 years, with average weight of 80 kg. By the time of examination diabetes mellitus was compensated, all patients received insulin in their necessary dosage. Neuroischemic form of "diabetic foot" was identified in all patients. The patients reported edema, pain, and easy fatigability at the level of their feet. Examination of skin revealed pigmentation, dryness of skin, hyperkeratosis, and reduced tactile sensitivity. In 35 patients, this disease was at the initial stage of pathologic process—no skin lesions were present.

The patients were randomly divided into two groups. The first group—control (17 subjects)—received basic therapy for insulin-dependent diabetes mellitus, the second group—main (18 subjects)—received dipeptide Thymogen L-Glu-L-Trp intramuscularly, daily, 200.0 µg 2 times a day, i.e., daily dose was 5 µg per kg of body weight (400.0 µg/80 kg), for 20 days (8.0 mg per treatment course) in addition to their basic therapy.

Effect of dipeptide Thymogen L-Glu-L-Trp on the clinical course of the complication of diabetes mellitus "diabetic foot", as well as its effect on the level of tissue oxygenation (according to the level of protein HIF-1α concentration in human blood plasma) were evaluated twice—in the beginning of the study and on the next day after the end of monitoring—on the 21st day. HIF-1α level was evaluated using an enzyme immunoassay (EIA) using a technique by A. Levina et al (see Levina A. A., Makeshova A. B., Mamukova Yu. I., Romanova E. A., Sergeeva A. I., Kazyukova T. V. Oxygen homeostasis regulation. Hypoxia induced factor (hif) and its role in oxygen homeostasis//Paediatria.-2009.-Vol. 87, No 4.-p. 92-97 (rus.)). Ten healthy volunteers who did not suffer from diabetes mellitus were involved as a supplementary control, whose venous blood was taken twice—on the first day of the study and on the 21st day—for determining the HIF-1α protein concentration level in blood plasma.

As can be seen from Table 5, patients with diabetes mellitus had a reliably higher value of protein HIF-1α concentration in blood plasma, which is an evidence of tissue ischemia. Initially, no reliable difference in this index was observed between the control and main groups. However, a reliable decrease in the concentration of HIF-1α protein was revealed in the blood plasma of main group patients against the background of L-Glu-L-Trp Thymogen dipeptide effect as compared to the control. The obtained data prove that the claimed substance has a capability of enhancing tissue oxygenation in case of complications of diabetes mellitus, in particular, diabetic foot.

TABLE 5

Effect of dipeptide Thymogen L-Glu-L-Trp on HIF-1α content in blood plasma

| Group | HIF-1α (pg/ml) | |
|---|---|---|
| | Initial index | Index on the 21st day |
| Healthy (n = 10) | 3.8 ± 0.3 | 3.9 ± 0.4 |
| Control group (n = 17) | 5.4 ± 0.6# | 5.7 ± 0.7# |
| Main group (n = 18) | 5.6 ± 0.5# | 4.5 ± 0.7*# | p < 0.05 - difference is statistically significant as compared to the index in healthy subjects.
*p < 0.05 - difference is statistically significant as compared to the initial index.

TABLE 6

Clinical signs of "diabetic foot" syndrome

| Clinical signs | Control group (n = 17) | | Main group (n = 18) | |
|---|---|---|---|---|
| | Before treatment | After treatment | Before treatment | After treatment |
| Pigmentation | 2.2 ± 0.41 | 2.2 ± 0.41 | 2.1 ± 0.25 | 2.1 ± 0.25 |
| Dryness of skin | 2.9 ± 0.33 | 3.2 ± 0.27 | 3.1 ± 0.25 | 2.5 ± 0.28* |
| Fatigability of feet | 3.3 ± 0.15 | 3.5 ± 0.25 | 3.4 ± 0.23 | 2.6 ± 0.30* |
| Tactile sensitivity (reduced) | 3.0 ± 0.22 | 3.2 ± 0.16 | 3.2 ± 0.29 | 2.4 ± 0.22* |

*p < 0.05 - difference is statistically significant as compared to the initial index in the control and experimental groups.

Characteristics of clinical signs:
1 point—absent
2 points—mild
3 points—pronounced
4 points—severe (strongly pronounced)

As can be seen from Table 6, clinical signs of "diabetic foot" syndrome were reliably reduced under the effect of dipeptide Thymogen L-Glu-L-Trp. Improved tissue oxygenation contributed to an improvement of trophic processes in tissues, which contributed to a reduction of foot fatigability in main group patients. It should be noted that tactile sensitivity was more or less restored in all patients who received dipeptide Thymogen L-Glu-L-Trp. Besides, skin structure was improved, which was manifested by reduced dryness of skin and restored skin color.

Thus, the claimed preparation—dipeptide Thymogen L-Glu-L-Trp- has a pronounced trophic effect by virtue of its capability of restoring tissue oxygenation processes.

Example 5

Efficacy of dipeptide Thymogen L-Glu-L-Trp use in the treatment of "diabetic foot" in patients with non-insulin-dependent diabetes mellitus.

Diabetes mellitus is known to negatively affect the course of lesion process by slowing down the healing of lesions. Therefore, such processes very often have a lingering, recurrent course.

Twenty-nine patients with non-insulin-dependent diabetes mellitus were monitored. All patients suffered from diabetes mellitus for 5 years-23 years and were 51 years old—82 years old. At the time of examination diabetes mellitus was compensated, all patients were treated with antihyperglycemic preparations in their necessary dosage.

Trophic lesions involving the skin, subcutaneous fat, muscles, without bone tissue damage, were revealed in all patients in the course of examination. Lesions were clean, non-infected. The patients complained of edema, moderate pain at the level of their lesions, and quick fatigability of their legs. Examination of skin revealed pigmentation, dryness of skin, hyperkeratosis, and significantly reduced tactile sensitivity. Visual evaluation of lesion surface was carried out in all patients, nature and phase of lesion process were determined, and standard treatment of lesion surface with antiseptic preparations was performed.

The patients were randomly divided into two groups. The first group—control (14 subjects)—received basic therapy with antihyperglycemic preparations and standard treatment of lesion surface, the second group—main (15 subjects)—received dipeptide Thymogen L-Glu-L-Trp intramuscularly, daily, 200.0 µg 2 times a day, for 20 days (8.0 mg per treatment course) in addition to their basic therapy.

Evaluation of dipeptide Thymogen L-Glu-L-Trp effect on the clinical course of diabetes mellitus complication—"diabetic foot", as well as its effect on the extent of tissue oxygenation (judging by HIF-1α protein concentration level in human blood plasma) was performed twice—in the beginning of the study and on the next day after the end of monitoring—on the 21st day. HIF-1α level was evaluated using an enzyme immunoassay (EIA) using the technique by A. Levina et al [24]. Ten healthy volunteers who did not suffer from diabetes mellitus were involved as a supplementary control, whose venous blood was taken twice-on the first day of study and on the 21st day, for determining protein HIF-1α concentration level in blood plasma.

TABLE 7

Effect of dipeptide Thymogen L-Glu-L-Trp on HIF-1α level in blood plasma

| Group | HIF-1α (pg/ml) | |
| --- | --- | --- |
| | Initial index | Index on the 21st day |
| Healthy (n = 10) | 3.8 ± 0.3 | 3.9 ± 0.4 |
| Control group (n = 14) | 6.7 ± 0.7# | 7.1 ± 0.5# |
| Main group (n = 15) | 6.9 ± 0.5# | 4.8 ± 0.4*# |

$p < 0.05$ - difference is statistically significant as compared to the index in healthy subjects.
*$p < 0.05$ - difference is statistically significant as compared to the initial index.

As can be seen from Table 7, patients with diabetes mellitus had a reliably higher value of protein HIF-1α concentration in blood plasma, which is an evidence of tissue ischemia. Initially, no reliable difference in this index was observed between the control and main groups. However, a reliable decrease in the concentration of HIF-1α protein by 30% was revealed in the blood plasma of main group patients against the background of L-Glu-L-Trp Thymogen dipeptide effect as compared to the control. The obtained data prove that the claimed substance has a capability of enhancing tissue oxygenation in case of complications of diabetes mellitus, in particular diabetic foot.

TABLE 8

Clinical signs of "diabetic foot" syndrome

| Clinical signs | Control group (n = 14) | | Main group (n = 15) | |
| --- | --- | --- | --- | --- |
| | Before treatment | After treatment | Before treatment | After treatment |
| Pigmentation | 3.3 ± 0.22 | 3.3 ± 0.22 | 3.0 ± 0.25 | 3.0 ± 0.25 |
| Dryness of skin | 3.8 ± 0.33 | 3.7 ± 0.29 | 3.9 ± 0.30 | 2.9 ± 0.29* |

TABLE 8-continued

Clinical signs of "diabetic foot" syndrome

| Clinical signs | Control group (n = 14) | | Main group (n = 15) | |
| --- | --- | --- | --- | --- |
| | Before treatment | After treatment | Before treatment | After treatment |
| Fatigability of feet | 3.8 ± 0.25 | 3.8 ± 0.29 | 3.9 ± 0.31 | 2.7 ± 0.35* |
| Tactile sensitivity (reduced) | 3.6 ± 0.22 | 3.7 ± 0.25 | 3.7 ± 0.22 | 2.5 ± 0.20* |

*$p < 0.05$ - difference is statistically significant as compared to the initial index in the control and experimental groups.

Characteristics of clinical signs:
1 point—absent
2 points—mild
3 points—pronounced
4 points—severe (strongly pronounced)

As can be seen from Table 8, clinical signs of "diabetic foot" syndrome were reliably reduced under the effect of dipeptide Thymogen L-Glu-L-Trp. Improved tissue oxygenation contributed to an improvement of trophic processes in tissues, which was evidenced by improved skin structure, reduced dryness of skin, restored tactile sensitivity, and reduced fatigability. These processes correlated with the rate of lesion surface healing in main group patients. So, by the end of the study, improved tissue oxygenation processes in 73.3% of patients contributed to full epithelization of lesion surface, which is 5 times greater than in the control (Table 9).

TABLE 9

Lesion surface healing stage on the 21st day of study

| Groups | Number of patients | | |
| --- | --- | --- | --- |
| | Signs of granulation | Initial epithelization signs | Full epithelization |
| Control (n = 14) | 5 (35.7%) | 7 (50.0%) | 2 (14.3) |
| Main (n = 15) | 1 (6.7%) | 3 (20.0%) | 11 (73.3) |

Thus, by virtue of its capability of restoring tissue oxygenation processes, the claimed preparation has a pronounced lesion healing effect as compared to standard therapy. Dipeptide Thymogen L-Glu-L-Trp shortens the term of lesion healing.

Clinical administration of dipeptide Thymogen L-Glu-L-Trp confirmed experimental data showing that the preparation is effective in case of diseases and conditions which are accompanied by ischemia and tissue oxygenation disorders.

The invention claimed is:

1. A method of enhancing tissue oxygenation by suppression of a hypoxia induced factor 1α (HIF-1α) in case of low oxygen tension in a tissue of a diabetic foot in a patient with type I or type II diabetes mellitus, the method comprising administering to the patient a dipeptide of L-glutamic acid-L-tryptophan (L-Glu-L-Trp).

2. A method of enhancing tissue oxygenation by suppression of a hypoxia induced factor 1α (HIF-1α) in case of low oxygen tension in a tissue of a diabetic foot in a patient with type I or type II diabetes mellitus, the method comprising locally administering to the patient a medical preparation comprising a dipeptide of L-glutamic acid-L-tryptophan (L-Glu-L-Trp) as an active agent and a pharmaceutically acceptable carrier, in a dose of 1.0 μg per kg-10.0 μg per kg of body weight of the patient at least once a day for a period necessary to achieve a therapeutic effect.

3. The method according to claim 2, wherein the medical preparation is in a form of a drug formulation.

4. The method according to claim 2, wherein the pharmaceutically acceptable carrier is a saline solution.

5. The method according to claim 2, wherein the period necessary to achieve the therapeutic effect is from 10 days to 40 days.

* * * * *